(12) United States Patent
Heki et al.

(10) Patent No.: US 7,392,200 B2
(45) Date of Patent: Jun. 24, 2008

(54) METHOD FOR RECOMMENDING DISPOSABLE ABSORBENT INCONTINENCE ARTICLES

(75) Inventors: Yukio Heki, Kobe Hyogo (JP); Tsutomu Kato, Kobe Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 508 days.

(21) Appl. No.: 10/733,560

(22) Filed: Dec. 11, 2003

(65) Prior Publication Data

US 2004/0122744 A1 Jun. 24, 2004

Related U.S. Application Data

(63) Continuation of application No. PCT/US02/17993, filed on Jun. 7, 2002.

(60) Provisional application No. 60/297,735, filed on Jun. 12, 2001.

(51) Int. Cl.
*A61B 5/00* (2006.01)
*A61B 5/20* (2006.01)

(52) U.S. Cl. .......................... 705/3; 128/920
(58) Field of Classification Search .................. 705/2, 705/3, 27, 1; 607/41; 128/920, 923, 898; 434/262; 706/924; 604/358, 367
See application file for complete search history.

(56) References Cited

U.S. PATENT DOCUMENTS

| | | | |
|---|---|---|---|
| 3,860,003 A | 1/1975 | Buell | |
| 4,695,278 A | 9/1987 | Lawson | |
| 4,795,454 A | 1/1989 | Dragoo | |
| 5,019,065 A | 5/1991 | Scripps | |
| 5,246,433 A | 9/1993 | Hasse | |
| 5,561,412 A | 10/1996 | Novak | |
| 5,569,234 A | 10/1996 | Buell | |
| 5,760,694 A | 6/1998 | Nissim | |
| 5,838,223 A | 11/1998 | Gallant | |
| 5,867,821 A * | 2/1999 | Ballantyne et al. | 705/2 |
| 5,937,387 A * | 8/1999 | Summerell et al. | 705/2 |
| 5,978,712 A | 11/1999 | Suda | |
| 6,014,631 A * | 1/2000 | Teagarden et al. | 705/3 |
| 6,269,339 B1 * | 7/2001 | Silver | 705/2 |
| 6,283,761 B1 * | 9/2001 | Joao | 434/236 |
| 2002/0096182 A1 * | 7/2002 | Hisanaka et al. | 128/898 |
| 2003/0046111 A1 * | 3/2003 | Snitkin | 705/2 |

(Continued)

FOREIGN PATENT DOCUMENTS

JP 10179768 A * 7/1998

(Continued)

*Primary Examiner*—Igor N Borissov
(74) *Attorney, Agent, or Firm*—Amanda T. Barry; Kevin C. Johnson; David M. Weirich

(57) ABSTRACT

The present invention is directed to a method for recommending a disposable absorbent incontinence article to be used by an incontinent person. The method includes the steps of: (a) receiving information, from a user, about incontinence devices which are currently used by the incontinent person; (b) receiving information about the situation which is experienced by the user; and (c) selecting at least one article, based on the information received, among predetermined disposable absorbent incontinence articles. By this method, an appropriate disposable absorbent incontinence article(s) to be used are recommended depending on the user's situation. The present invention is also directed a method for evaluating the quality of life of a caregiver who takes care of an incontinent person.

9 Claims, 3 Drawing Sheets

U.S. PATENT DOCUMENTS

2003/0171954 A1 * 9/2003 Guerin et al. ............. 705/2
2004/0049408 A1 * 3/2004 Voss et al. ................ 705/3

FOREIGN PATENT DOCUMENTS

| WO | WO 99/00086 A1 | 1/1999 |
| WO | WO 00/00113 A1 | 1/2000 |
| WO | WO 02/100292 A2 * | 12/2002 |

* cited by examiner

METHOD FOR RECOMMENDING DISPOSABLE ABSORBENT INCONTINENCE ARTICLES

CROSS REFERENCE TO RELATED APPLICATIONS

This application is a continuation of PCT/US02/17993 filed on 7 Jun. 2002, which claims the benefit of U.S. Provisional Application No. 60/297,735 filed on 12 Jun. 2001.

FIELD

The present invention generally relates to computer based methods for providing information, and particularly to a method for recommending a disposable absorbent incontinence article to be used by an incontinent person. The recommendation is based on information about the user's situation which is received preferably through a network.

BACKGROUND

The Internet has developed rapidly over the past several years, and is known as a very useful tool for obtaining and/or providing various information. Many people or companies who want to provide certain information about their businesses have a web site which is accessible by customers or clients (i.e., Internet users) through the Internet. The Internet users can obtain information by visiting web sites which are chosen by inputting web site addresses. For example, consumer product companies (e.g., The Procter & Gamble Company) have their own web sites (e.g., at an Internet address: http://www.pg.com/) which can provide information about their products as well as other information. Consumers can obtain necessary or desired information about their products by accessing to the web site through the Internet.

It is generally recognized in many countries (e.g., Japan) that the number of the aged people has been and/or will be increasing. It is also anticipated that the number of incontinent persons who need caregivers' helps will be increasing. It is generally understood that the increase of incontinent persons (in particular adult incontinent persons) significantly affects people's lives not only for the incontinent persons but also caregivers who take care of such incontinent persons. Caregivers tend to face various issues when taking care of incontinent persons. These issues are not same and very dependent on caregivers' situations since the conditions of their incontinent persons are different individually. This fact tends to result in lack of appropriate information for caregivers to take care of incontinent persons appropriately. For example, while a caregiver needs information about a disposable absorbent article(s) and/or an adult incontinence device (s) which is most appropriate to his/her incontinent person or situation, the caregiver can not easily access to and thus get appropriate information which best meets the needs. Examples of information about a disposable absorbent article (s) needed by users herein include the brand names, kinds and types, and sellers' names of disposable absorbent articles, their usage instruction, and general educational information for taking care of incontinent persons by using the disposable absorbent article(s). These types of information is needed since they are not sufficient even among professional caregivers such as home helpers, nurses and social workers as well as professional advisers such as pharmacists and medical doctors.

In addition, although the caregivers' burden is generally recognized as a big issue, there is no method for evaluating the same. Such a measurement is important since if there is too much burden for a caregiver, there may be an issue in the manner and/or the quality for taking care of his/her incontinent person, for example, an inappropriate selection and/or use of disposable absorbent incontinence articles and/or incontinence devices, an inappropriate method for taking care of the incontinent person, and the like.

Based on the foregoing, there is a need for users of incontinence devices to provide recommendation of appropriate disposable absorbent incontinence articles to be used based on their situations. There is also a need for users of incontinence devices to provide recommendation of an appropriate combination of two (or more) disposable absorbent incontinence articles to be used based on their situations thereby making the care easier and more effective. There is further a need to analyze caregivers' quality of lives and provide recommendation for improving the same.

SUMMARY

The present invention is directed to a method for recommending a disposable absorbent incontinence article to be used by an incontinent person. The method comprises the steps of: (a) receiving information, from a user, about incontinence devices which are currently used by the incontinent person; (b) receiving information about the situation which is experienced by the user; and (c) selecting at least one article, based on the information received, among predetermined disposable absorbent incontinence articles.

The present invention is also directed a method for evaluating the quality of life of a caregiver who takes care of an incontinent person. The method comprises the steps of: (a) receiving information about an average free time the caregiver can have within a day; (b) receiving information about a degree of physical burden the caregiver has for taking care of the incontinent person; (c) receiving information about a degree of mental burden the caregiver has for taking care of the incontinent person; and (d) calculating a value of the quality of life (QOL) based on the received information in accordance with a predetermined algorism.

The foregoing answers the need for users of incontinence devices to provide recommendation of appropriate disposable absorbent incontinence articles to be used depending on their situations. The foregoing also answers need to analyze caregivers' quality of lives and provide recommendation for improving the same.

These and other features, aspects, and advantages of the present invention will become evident to those skilled in the art from reading of the present disclosure.

BRIEF DESCRIPTION OF THE DRAWINGS

While the specification concludes with claims particularly pointing out and distinctly claiming the invention, it is believed that the invention will be better understood from the following description of preferred embodiments taken in conjunction with the accompanying drawings wherein like designations are used to designate substantially identical elements, and in which:

DETAILED DESCRIPTION

Figure 1:
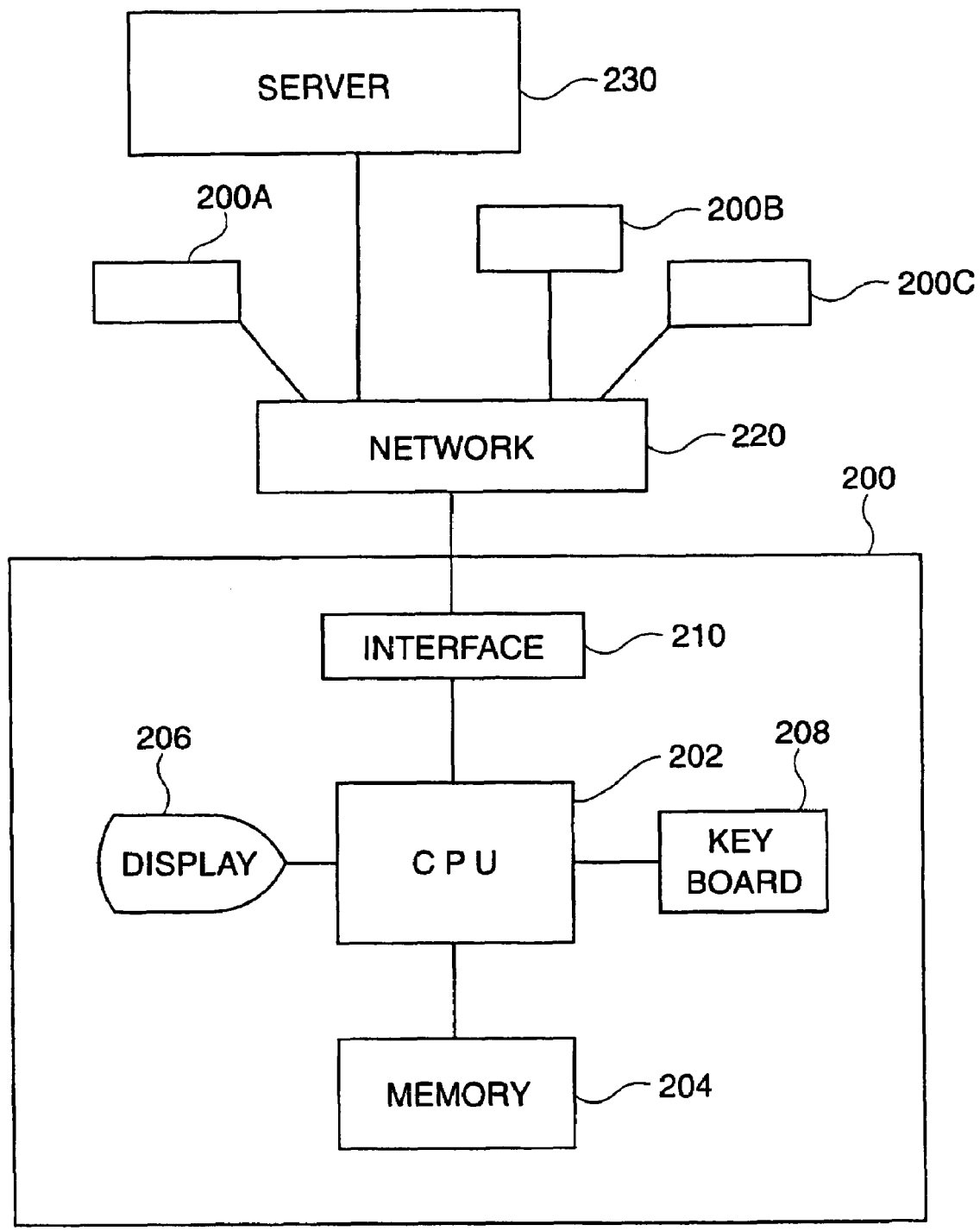
FIG. 1 is a block diagram of a product recommendation system (or device) which is one preferred embodiment of the present invention.

All cited references are incorporated herein by reference in their entirety. Citation of any reference is not an admission regarding any determination as to its availability as prior art to the claimed invention.

Herein, the terms "comprise", "include" and "contain" mean that other element(s) and step(s) which do not affect the end result can be added. These terms encompass the terms "consisting of" and "consisting essentially of".

Herein, the term "incontinence device" refers to devices which are used for taking care of an incontinent person for incontinence care purposes. Examples of incontinence devices include disposable absorbent incontinence articles, non-disposable absorbent incontinence articles (e.g., cloth diapers, diaper covers and incontinence shorts), portable toilets, urinals, and vacuum incontinence take-away devices.

Herein, the term "absorbent article" refers to articles which absorb and contain body exudates, and more specifically, refers to devices which are placed against or in proximity to the body of the wearer to absorb and/or contain the various body fluids or exudates discharged from the body.

Herein, the term "disposable" is used to describe absorbent articles which are not intended to be laundered or otherwise restored or reused as an absorbent article (i.e., they are intended to be discarded after a single use and, preferably, to be recycled, composted or otherwise disposed of in an environmentally compatible manner).

Herein, the term "disposable absorbent incontinence article" refers to disposable absorbent articles which are designed to be preferably used by incontinent persons. Preferred disposable absorbent incontinence articles include disposable taped diapers, disposable pull-on diapers, disposable urine incontinence pads, disposable flat pads, disposable faecal collector pouches, and disposable urine collector pouches.

Herein, the term "disposable taped diaper" refers to disposable absorbent incontinence articles generally having a hourglass outline shape which is drawn up between the legs and fastened about the waist of the wearer by means of a pair of tape fasteners. The tape fastener can be either an adhesive fastener type or a mechanical fastener type. Examples of disposable taped diapers are disclosed in U.S. Pat. No. 3,860,003 issued to Buell on Jan. 14, 1975; U.S. Pat. No. 4,695,278 issued to Lawson on Sep. 22, 1987; U.S. Pat. No. 4,795,454 issued to Dragoo on Jan. 3, 1989; and U.S. Pat. No. 5,019,065 issued to Scripps on May 18, 1991. In a preferred embodiment, the disposable taped diaper has a fluid absorbent capacity of about 600 cc. A preferred disposable taped diaper is marketed by Procter & Gamble Far East, Inc. in Japan under the trade name "Attento Tape-shiki".

Herein, the term "disposable pull-on diaper" refers to disposable absorbent incontinence articles having two leg openings and a waist opening which are drawn up between the legs and fastened about the waist of the wearer by means of an elastic waistband which is typically disposed along the waist opening. Examples of disposable pull-on diapers are disclosed in U.S. Pat. No. 5,246,433 issued to Hasse et al. on Sep. 21, 1993; and U.S. Pat. No. 5,569,234 issued to Buell et al. on Oct. 29, 1996. In a preferred embodiment, there are two types of disposable pull-on diapers for an incontinence use. One type is called "light" or "daytime use" and has a fluid absorbent capacity of from about 200 cc to about 400 cc. The other type is called "severe" or "nighttime use" and has a fluid absorbent capacity of from about 400 cc to about 600 cc. One preferred disposable pull-on diaper for "light" or "daytime use" is marketed by Unicharm Corporation in Japan under the trade name "Lifree Rehabili-Pant Usugata-Keikai type". A preferred disposable pull-on diaper for "severe" or "nighttime use" is marketed by Procter & Gamble Far East, Inc. in Japan under the trade name "Attento Anshin Kyushu Pant".

Herein, the term "disposable urine incontinence pad" refers to disposable absorbent incontinence articles generally having a rectangular or calabash outline shape which are used together with another article which holds the pad such as a disposable taped diaper and a disposable pull-on diaper. The disposable urine incontinence pad may also be referred to as "disposable supplemental pad", "S-pad" or "urine take-away pad". The disposable urine incontinence pad is placed between the body of the wearer and the diaper. The disposable urine incontinence pad may be used alone (i.e., without another article that holds the same) in a normal undergarment such as shorts for a light incontinent person. In a preferred embodiment, there are two types of disposable urine incontinence pads for an incontinence use. One type is called "regular", "super" or "daytime use" which has a length of from about 400 mm to about 550 mm, a width about 200 mm, and a fluid absorbent capacity of from about 150 cc to about 300 cc. The other type is called "big", "wide" or "nighttime use" which has a length of about 550 mm (or more), a width from about 200 to about 300 mm, and has a fluid absorbent capacity of from about 300 cc to about 700 cc. A preferred disposable urine incontinence pad for "regular", "super" or "daytime use" is marketed by Procter & Gamble Far East, Inc. in Japan under the trade name "Attento Nyotori Pad". A preferred disposable urine incontinence pad for "big", "wide" or "nighttime use" is marketed by Hakujuji Co. Ltd., in Japan under the trade name "Salva Overnight Pad".

Herein, the term "disposable flat pad" refers to disposable absorbent incontinence articles generally having a rectangular outline shape which are used together with a diaper cover. The disposable flat pad is placed between the body of the wearer and the diaper cover. In a preferred embodiment, the disposable flat pad has a fluid absorbent capacity of from about 200 cc to about 400 cc. A preferred disposable flat pad is marketed by Hakujuji Co. Ltd., in Japan under the trade name "Salva LLD".

Herein, the term "guard" refers to absorbent incontinence articles generally having a rectangular or calabash outline shape which are used together with a normal undergarment such as shorts. The guard is placed between the body of the wearer and the underwear. In a preferred embodiment, the guard has a fluid absorbent capacity of from about 50 cc to about 150 cc. A preferred guard is marketed by Crecia Corporation in Japan under the trade name "Poise Pad".

Herein, the term "disposable faecal collector pouch" refers to disposable pouches having an opening and an anatomically-shaped glue flange which surrounds the opening. The disposable faecal collector pouch is applied to a wearer to cover and adhere to the anus area through the glue flange. Examples of disposable faecal collector pouches are disclosed in International Publication No. WO 99/00086.

Herein, the term "disposable urine collector pouch" refers to disposable pouches having an opening and an anatomically-shaped glue flange which surrounds the opening. The disposable urine collector pouch is applied to a wearer to cover and adhere to the urogenital area or the external genitalia area through the glue flange. Examples of disposable urine collector pouches are disclosed in International Publication No. WO 00/00113.

Herein, the term "user" refers to people who actually use (or wear) an incontinence device and/or caregivers who take care of an incontinent person. The caregiver can be either professional or non-professional. The professional caregiver includes, for example, a nurse, a home helper, a care-manager, and a medical doctor. A typical non-professional caregiver is a family member of the incontinent person.

FIG. 1 is a block diagram of a product recommendation system (or device) which recommends a disposable absorbent incontinence article, which is one preferred embodiment of the present invention. Referring to FIG. 1, a product recommendation device 200 includes a data processing means or a central processing unit (CPU) 202; a data storage means or a memory unit 204; an output means or a display unit 206; and a data or information input means or a key board 208. A user of the product recommendation device 200 inputs necessary data or information through the key board 208. As is described in detail hereinafter, the CPU 202 performs necessary data processing with respects to the input data in accordance with a program(s) which is stored in the memory unit 204. The resultant data is also stored in the memory unit 204, and if desired, is shown to the user through the display unit 206. In one preferred embodiment, the product recommendation system is implemented by a stand-alone computer or device (i.e., the device 200) which is not connected to any communication or computer network system.

In a more preferred embodiment, the product recommendation system is implemented by a network system wherein a server computer 230 and client computers 200 and 200A-200C are connected to the product recommendation device 200 through a network. In this embodiment, the product recommendation device 200 further includes an interface unit 210 which is connected to the server computer 230 through a network 220. Herein, the term "network" encompasses both a communication network and a computer network. Herein, the term "computer network" refers to a network which includes at least two, and preferably a number of computers or devices connected through a communication line or a communication network. The communication line or network can be either wired or wireless. Preferred examples of the computer networks include a Local Area Network (LAN), the Internet, and variations on the Internet such as a Wireless Access Protocol (WAP) network, a mobile phone network (e.g., i-mode®) and the like.

In the embodiment shown in FIG. 1, the input data by a user can be sent, through the computer network 220, to the server computer 230 which performs necessary data processing of the present invention with respects to the data or information inputted by users in accordance with a program(s) which is stored in the server computer 230. The resultant data is stored in the server computer 230, and is also sent to the device 200 through the computer network 220 to display the same in the display unit 206. Other product recommendation devices 200A, 200B and 200C which are used by other users can be connected to the server computer 230 through the computer network 220 so that the server computer 230 can provide the same service for the other users.

Figure 2:
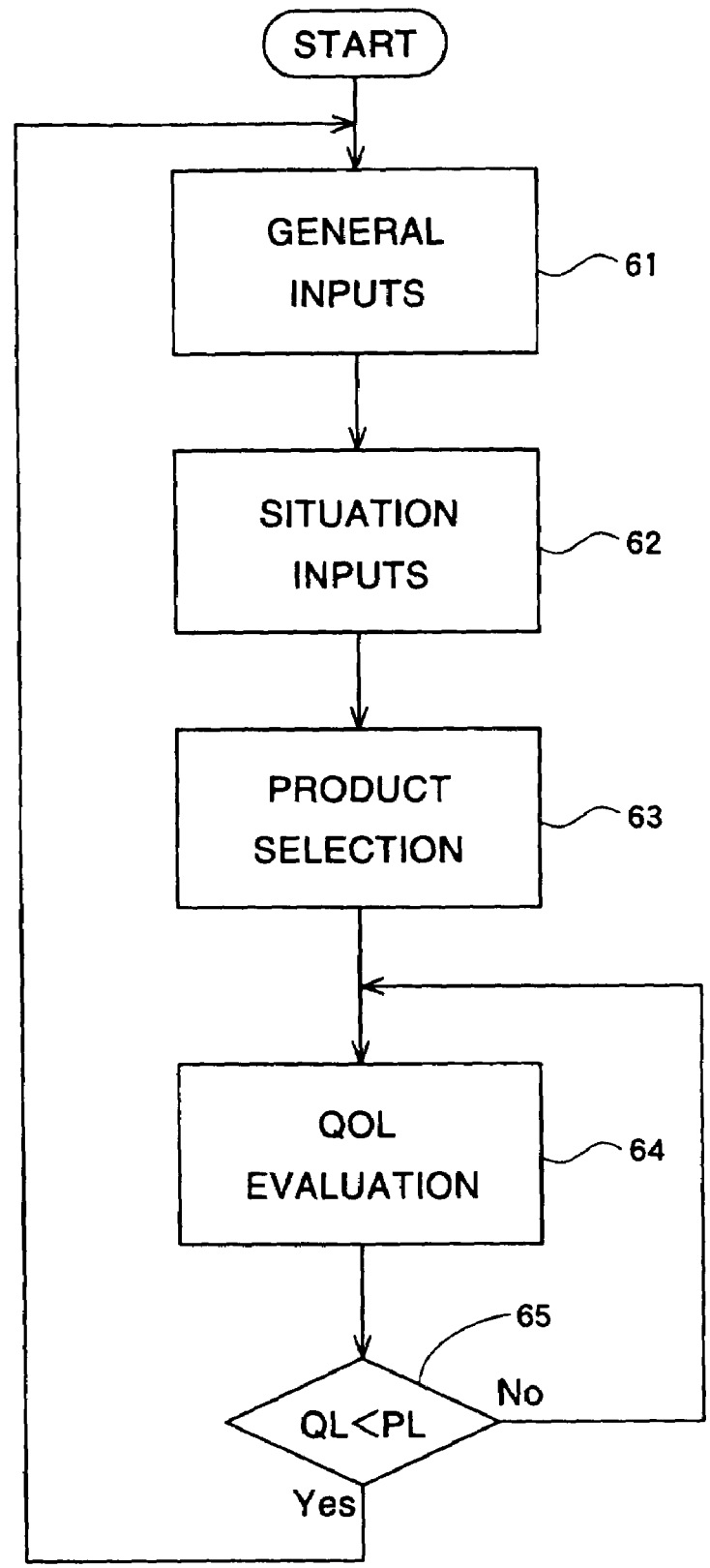
FIG. 2 is a flow chart describing the processes which is performed by the product recommendation system shown in FIG. 1.

FIG. 2 is a flow chart which shows the general operation of the product recommendation system shown in FIG. 1.

In Step 61, general information about a user (i.e., an incontinent person and/or a caregiver) is inputted by the user and received by the system. The general information about the user includes, for example, the user's name, the users' ID numbers, the e-mail address and phone number, the incontinent person's sex and age, the care level of the incontinent person in the care-insurance, the service provider's name, the interviewer's (or the data entry person's) name, and a specific time period (preferably within one day) the user wants to consider by using the product recommendation system. The general information about the user also includes the information about incontinence devices which are currently used by the incontinent person.

In Step 62, information about the situation which is experienced by the user is inputted by the user and received by the system. The information about the situation experienced by the user can include any information about the situation the incontinent person and/or the caregiver actually experiences when using the incontinence devices including disposable absorbent incontinence articles in daily lives.

In Step 63, based on the information received, at least one disposable absorbent incontinence article is selected among predetermined disposable absorbent incontinence articles by the system. The predetermined disposable absorbent incontinence articles preferably include disposable taped diapers, disposable pull-on diapers, disposable urine incontinence pads, disposable flat pads, disposable faecal collector pouches, and disposable urine collector pouches. The resultant information about the product recommendation is sent to the user through the network automatically. If desired, other information such as usage instruction for the recommended disposable absorbent incontinence article(s), information about the other incontinence device(s) and general (or specific if appropriate) advices for taking care of the incontinent person is also sent together with the product recommendation.

In a preferred embodiment, the quality of life of a caregiver who takes care of the incontinent person is evaluated (or calculated) by the system (in Step 64), and the value of the caregiver's quality of life (QOL) which is obtained by the calculation is sent to the user through the network. The calculation of the caregiver's quality of life is performed periodically (e.g., once for about 3 months) by periodically repeating Step 64 and the value of the quality of life (QOL) is monitored by the system. If the value of the quality of life (QOL) is below a predetermined level PL (Step 65), the process returns to Step 61 and necessary processes for modified product recommendation is performed by repeating Steps 61, 62 and 63. The resultant modified product recommendation is also sent to the user through the network.

In preferred embodiments, the system has (or stores) predetermined questions to be asked to users. The system also has a plurality of predetermined possible answers, for each question, for selection by users. The use of these predetermined questions and predetermined possible answers is preferred to receive necessary information with minimum inputs by users. Table I shows an example of a data structure for such predetermined questions and predetermined possible answers. In this example, there are in total m predetermined questions Q1-Qm each of which has a different number of predetermined possible answers PA which are to be selected by users. For example, the i-th question Qi has in total j of possible answers PA(i,1)-PA(i,j). The total number j of possible answers for each question is decided depending on the system design. The total number m of the predetermined questions is also decided depending on the system design.

TABLE I

| Q1 | PA(1,1) | PA(1,2) | — | — | — | — |
|---|---|---|---|---|---|---|
| Q2 | PA(2,1) | PA(2,2) | PA(2,3) | PA(2,4) | — | — |
| Q3 | PA(3,1) | PA(3,2) | PA(3,3) | PA(3,4) | PA(3,5) | PA(3,6) |
| Q4 | PA(4,1) | PA(4,2) | PA(4,3) | — | — | — |
| . | . | . | . | . | . | . |

TABLE I-continued

| | | | | | | |
|---|---|---|---|---|---|---|
| . | . | . | . | . | . | . |
| Qi | PA(i,1) | . | PA(i,j) | — | — | — |
| . | . | . | . | . | . | . |
| . | . | . | . | . | . | . |
| . | . | . | . | . | . | . |
| Qm | PA(m,1) | PA(m,2) | PA(m,3) | PA(m,4) | PA(m,5) | — |

Tables II (a)-(j) show an example of questions and possible answers which are used in a preferred embodiment. This example includes questions Q1-Q22 and possible answers PA(1,1)-PA(22,4).

It should be noted that these questions and possible answers are merely examples, and depending on the system design one or more of them may be eliminated and/or any other questions and possible answers can be used as long as they can help the system to understand the user's situation. (In Tables II (a)-(j), "IP" stands for an incontinent person.)

In a preferred embodiment, the information about the user's situation is on the availability and/or the quality of the caregiving. Such information can be preferably obtained by using the question Q2 and its possible answers in Table II (a).

TABLE II (a)

| Q1: Sex of Incontinent Person (IP) | Q2: Availability of Care Giver |
|---|---|
| PA(1,1): male | PA(2,1): enough both for quantity and quality |
| PA(1,2): female | PA(2,2): enough for quantity but not for quality |
| | PA(2,3): enough for quality but not for quantity |
| | PA(2,4): not enough both for quantity and quality |

In a preferred embodiment, the information about the user's situation is also on the incontinent person's self-recognition for incontinence of urine. Such information can be preferably obtained by using the question Q3 and possible answers in Table II (b).

Preferably, the information about the user's situation is also on the incontinent person's tendency for removal of a disposable absorbent article (e.g., a diaper). Such information can be preferably obtained by using the question Q4 and possible answers in Table II (b).

TABLE II (b)

| Q3: IP's Self-Recognition for Urine Incontinene | Q4: IP's Tendency for Removal of Diaper |
|---|---|
| PA(3,1): very low | PA(4,1): not remove by oneself |
| PA(3,2): somewhat low | PA(4,2): remove by oneself when should not |
| PA(3,3): almost normal | PA(4,3): remove by oneself when should |
| PA(3,4): normal | |

In a preferred embodiment, the information about the user's situation is on the ability of activity in daily living (often referred to as "ADL") of an incontinent person. Preferably, the information about the user's situation is on the ability of body action of an incontinent person. Such information can be preferably obtained by using the question Q5 and possible answers in Table II (c). More preferably, the information about the user's situation is on the ability of hand/finger activity of an incontinent person. Such information can be preferably obtained by using the question Q6 and possible answers in Table (c).

TABLE II (c)

| Q5: IP's Body Ability | Q6: IP's Hand/Finger Ability |
|---|---|
| PA(5,1): bedridden | PA(6,1): can not grasp any |
| PA(5,2): can lift the hip/lie at side | PA(6,2): can move one hand but not grasp any |
| PA(5,3): can sit | PA(6,3): can move one hand and can grasp any |
| PA(5,4): can stand | PA(6,4): can move both hands but not grasp any |
| PA(5,5): can walk slowly | PA(6,5): can move both hands and grasp any |
| PA(5,6): can walk | |

In a preferred embodiment, the information about the user's situation is on the body form balance of an incontinent person. Such information can be preferably obtained by using the question Q7 and possible answers in Table II (d).

Preferably, the information about the user's situation is on the body set of the incontinent person. Such information can be preferably obtained by using the question Q8 and possible answers in Table II (d).

TABLE II (d)

| Q7: IP's Body Form Balance | Q8: IP's Body Set |
|---|---|
| PA(7,1): thinner at thighs and normal waist | PA(8,1): can not open legs due to body set |
| PA(7,2): big and/or fat | PA(8,2): can not bend leg due to set |
| PA(7,3): normal | PA(8,3): no body set |

In a preferred embodiment, the information about the user's situation is on the contents of leakage of an incontinent person. Such information can be preferably obtained by using the question Q9 and possible answers in Table II (e).

Preferably, the information about the user's situation is on when and/or how urine incontinence occurs. Such information can be preferably obtained by using the question Q10 and possible answers in Table II (e).

TABLE II (e)

| Q9: Contents of Leakage | Q10: When/How Urine Incontinence Occur |
|---|---|
| PA(9,1): urine only | PA(10,1): not known |
| PA(9,2): feces only | PA(10,2): stringingly |
| PA(9,2): both urine and feces | PA(10,3): within short period after desire of urination |
| | PA(10,4): when pressure applied to stomach |

In a preferred embodiment, the information about the user's situation is on the discharging speed of urine of an incontinent person. Such information can be preferably obtained by using the question Q11 and possible answers in Table II (f).

Preferably, the information about the user's situation is on the discharging amount of urine into a disposable absorbent article (e.g., a diaper). Such information can be preferably obtained by using the question Q12 and possible answers in Table II (f).

TABLE II (f)

| Q11: Urine Discharging Speed | Q12: Discharged Amount Into Diaper (Urine) |
|---|---|
| PA(11,1): not known | PA(12,1): all |
| PA(11,2): trickle | PA(12,2): about half |
| PA(11,3): low speed | PA(12,3): some but the rest is into toilet |

TABLE II (f)-continued

| Q11: Urine Discharging Speed | Q12: Discharged Amount Into Diaper (Urine) |
|---|---|
| PA(11,4): high speed | PA(12,4): a little but the most is into toilet<br>PA(12,5): fundamentally all is into toilet<br>PA(12,6): all is into toilet |

In a preferred embodiment, the information about the user's situation is on the kind and/or type of a disposable absorbent article(s) used by an incontinent person. Such information can be preferably obtained by using the question Q13 and possible answers in Table II (g).

Preferably, the information about the user's situation is on the changing frequency of disposable absorbent articles within the specified time period, preferably within one day (e.g., from 7:00 am to 10:00 pm). Such information can be preferably obtained by using the question Q14 and possible answers in Table II (g).

TABLE II (g)

| Q13: Absorbent Article Used | Q14: Changing Frequency |
|---|---|
| PA(13,1): S-pad (regular/super) | PA(14,1): 1-2 articles |
| PA(13,2): S-pad (big/night) | PA(14,2): 3-4 articles |
| PA(13,3): Pull-on diaper (light/daytime) | PA(14,3): 5-6 articles |
| PA(13,4): Pull-on diaper (severe/nighttime) | PA(14,4): 7-8 articles |
| PA(13,5): Taped diaper | PA(14,5): more than 8 articles |
| PA(13,6): Flat pad | |
| PA(13,7): Guard/Light incontinence pad | |
| PA(13,8): Belted undergarment | |

In a preferred embodiment, the information about the user's situation is on the discharged amount of urine per one disposable absorbent article by an incontinent person. Such information can be preferably obtained by using the question Q15 and possible answers in Table II (h). This information is used to calculate the amount of urine discharged by the incontinent person for one day as described hereinafter.

Preferably, the information about the user's situation is on the position of a gap formed if any between the body of the wearer and a disposable absorbent article which is worn by an incontinent person. Such information can be preferably obtained by using the question Q18 and possible answers in Table II (h).

TABLE II (h)

| Q15: Discharged Amount Per Article | Q18: Gap Position Between Body and Absorbent Article |
|---|---|
| PA(15,1): full (wet widely and heavily) | PA(18,1): at legs |
| PA(15,2): half (wet about half) | PA(18,2): at waist |
| PA(15,3): quarter or below (wet a little) | PA(18,3): no gap |

In a preferred embodiment, the information about the user's situation is on the position of a leakage if any from a disposable absorbent article worn by an incontinent person. Such information can be preferably obtained by using the question Q19 and possible answers in Table II (i). The term "front-center" means a leakage of urine and/or feces occurs around the center portion in the front panel of a disposable absorbent incontinence article. The term "back-center" means a leakage occurs around the center portion in the back panel of a disposable absorbent incontinence article. The term "leg(s)" means a leakage occurs around the leg opening portion(s) of a disposable absorbent incontinence article. The term "side(s)" means a leakage occurs around the side (or ear) panel portion(s) of a disposable absorbent incontinence article.

Preferably, the information about the user's situation is on the position of a gap formed if any between the body of the wearer and a disposable absorbent article which is worn by an incontinent person. Such information can be preferably obtained by using the question Q18 and possible answers in Table II (i).

TABLE II (i)

| Q19: Leakage Position | Q20: Discharged Amount Into Diaper (Feces) |
|---|---|
| PA(19,1): front-center | PA(20,1): all |
| PA(19,2): back-center | PA(20,2): about half |
| PA(19,3): leg(s) | PA(20,3): some but the rest is into toilet |
| PA(19,4): side(s) | PA(20,4): a little but the most is into toilet |
| | PA(20,5): fundamentally all is into toilet |
| | PA(20,6): all is into toilet |

In a preferred embodiment, the information about the user's situation is on the frequency of feces which are discharged by an incontinent person into a disposable absorbent article(s). Such information can be preferably obtained by using the question Q21 and possible answers in Table II (j).

Preferably, the information about the user's situation is on the discharged amount of feces which are discharged by an incontinent person for one time. Such information can be preferably obtained by using the question Q22 and possible answers in Table II (j).

TABLE II (j)

| Q21: Frequency of Feces discharged into Article | Q22: Discharged Amount at Once (Feces) |
|---|---|
| PA(21,1): more than once a day | PA(22,1): large (more than 2 fists) |
| PA(21,2): once per 2-3 days | PA(22,2): normal (about a fist) |
| PA(21,3): once per 4-6 days | PA(22,3): small (about 2 fingers) |
| PA(21,4): less than once a week | PA(22,4): just a line on a garment |
| | PA(22,5): no feces discharged into a garment |

One user is requested to answer preferably all the questions by choosing one answer among the possible answers. However, it should be noted that the questions and possible answers in Tables (a)-(j) are merely preferred examples and other questions and possible answers can be used. The user's answers constitute the information about the situation experienced by the user. Based on the answers, the product recommendation system understands the user's situation.

In a preferred embodiment, the information about the user's situation is on the amount of urine discharged by the incontinent person for a certain time period. Such a certain time period can be specified by either the user or the system (automatically). Preferably, the time period is specified by the user (e.g., from 7:00 am to 10:00 pm). The amount of urine discharged is preferably obtained by using a predetermined calculation method based on the information (i.e., the answers) obtained in response to the questions Q13, Q14 and Q15. Such a calculation is preferably performed by referring to Tables III (a)-(g), although any other calculation manner known in the art can be used. These tables show, for each absorbent article, estimated amounts of urine discharged by an incontinent person based on the frequency of changes of the articles within the time period specified by the user. (In Tables III (a)-(g), "COF" stands for a coefficient which is multiplied by the full (or a half, or a quarter of the full) absorbency of a disposable absorbent incontinence article to produce an estimated amount of urine.) It should be noted that the amount of urine discharged for a certain time period can be measured or calculated by using other methods if any known in the art.

TABLE III (a)

(Disposable Taped Diaper)

| Frequency of Change | Full (500 cc) | | | | | Half (250 cc) | | | | | Quarter (125 cc) | | | | |
|---|---|---|---|---|---|---|---|---|---|---|---|---|---|---|---|
| | 1~2 | 3~4 | 5~6 | 7~8 | 9~ | 1~2 | 3~4 | 5~6 | 7~8 | 9~ | 1~2 | 3~4 | 5~6 | 7~8 | 9~ |
| COF. | 1.5 | 3.5 | 5.5 | 7.5 | 10 | 1.5 | 3.5 | 5.5 | 7.5 | 10 | 1.5 | 3.5 | 5.5 | 7.5 | 10 |
| Amount of Urine | 750 | 1750 | 2750 | 3750 | 5000 | 375 | 875 | 1375 | 1875 | 2500 | 187.5 | 437.5 | 687.5 | 937.5 | 1250 |

TABLE III (b)

(Disposable Pull-on Diaper (Light/Daytime))

| Frequency of Change | Full (250 cc) | | | | | Half (125 cc) | | | | | Quarter (62.5 cc) | | | | |
|---|---|---|---|---|---|---|---|---|---|---|---|---|---|---|---|
| | 1~2 | 3~4 | 5~6 | 7~8 | 9~ | 1~2 | 3~4 | 5~6 | 7~8 | 9~ | 1~2 | 3~4 | 5~6 | 7~8 | 9~ |
| COF. | 1.5 | 3.5 | 5.5 | 7.5 | 10 | 1.5 | 3.5 | 5.5 | 7.5 | 10 | 1.5 | 3.5 | 5.5 | 7.5 | 10 |
| Amount of Urine | 375 | 875 | 1375 | 1875 | 2500 | 187.5 | 437.5 | 687.5 | 937.5 | 1250 | 93.75 | 218.75 | 343.75 | 468.75 | 625 |

TABLE III (c)

(Disposable Pull-on Diaper (Severe/Nighttime))

| Frequency of Change | Full (500 cc) | | | | | Half (250 cc) | | | | | Quarter (125 cc) | | | | |
|---|---|---|---|---|---|---|---|---|---|---|---|---|---|---|---|
| | 1~2 | 3~4 | 5~6 | 7~8 | 9~ | 1~2 | 3~4 | 5~6 | 7~8 | 9~ | 1~2 | 3~4 | 5~6 | 7~8 | 9~ |
| COF. | 1.5 | 3.5 | 5.5 | 7.5 | 10 | 1.5 | 3.5 | 5.5 | 7.5 | 10 | 1.5 | 3.5 | 5.5 | 7.5 | 10 |
| Amount of Urine | 750 | 1750 | 2750 | 3750 | 5000 | 375 | 875 | 1375 | 1875 | 2500 | 187.5 | 437.5 | 687.5 | 937.5 | 1250 |

TABLE III (d)

(Disposable Urine incontinence pad (Regular/Super))

| Frequency of Change | Full (200 cc) | | | | | Half (100 cc) | | | | | Quarter (50 cc) | | | | |
|---|---|---|---|---|---|---|---|---|---|---|---|---|---|---|---|
| | 1~2 | 3~4 | 5~6 | 7~8 | 9~ | 1~2 | 3~4 | 5~6 | 7~8 | 9~ | 1~2 | 3~4 | 5~6 | 7~8 | 9~ |
| COF. | 1.5 | 3.5 | 5.5 | 7.5 | 10 | 1.5 | 3.5 | 5.5 | 7.5 | 10 | 1.5 | 3.5 | 5.5 | 7.5 | 10 |
| Amount of Urine | 300 | 700 | 1100 | 1500 | 2000 | 150 | 350 | 550 | 750 | 1000 | 75 | 175 | 275 | 375 | 500 |

TABLE III (e)

(Disposable Urine incontinence pad (Overnight/Big/Wide))

| Frequency of Change | Full (400 cc) | | | | | Half (200 cc) | | | | | Quarter (100 cc) | | | | |
|---|---|---|---|---|---|---|---|---|---|---|---|---|---|---|---|
| | 1~2 | 3~4 | 5~6 | 7~8 | 9~ | 1~2 | 3~4 | 5~6 | 7~8 | 9~ | 1~2 | 3~4 | 5~6 | 7~8 | 9~ |
| COF. | 1.5 | 3.5 | 5.5 | 7.5 | 10 | 1.5 | 3.5 | 5.5 | 7.5 | 10 | 1.5 | 3.5 | 5.5 | 7.5 | 10 |
| Amount of Urine | 600 | 1400 | 2200 | 3000 | 4000 | 300 | 700 | 1100 | 1500 | 2000 | 150 | 350 | 550 | 750 | 1000 |

TABLE III (f)

| | (Disposable Flat Pad) | | | | | | | | | | | | | | |
|---|---|---|---|---|---|---|---|---|---|---|---|---|---|---|---|
| | Full (250 cc) | | | | | Half (125 cc) | | | | | Quarter (62.5 cc) | | | | |
| Frequency of Change | 1~2 | 3~4 | 5~6 | 7~8 | 9~ | 1~2 | 3~4 | 5~6 | 7~8 | 9~ | 1~2 | 3~4 | 5~6 | 7~8 | 9~ |
| COF. | 1.5 | 3.5 | 5.5 | 7.5 | 10 | 1.5 | 3.5 | 5.5 | 7.5 | 10 | 1.5 | 3.5 | 5.5 | 7.5 | 10 |
| Amount of Urine | 375 | 875 | 1375 | 1875 | 2500 | 187.5 | 437.5 | 687.5 | 937.5 | 1250 | 93.75 | 218.75 | 343.75 | 468.75 | 625 |

TABLE III (g)

| | (Guard) | | | | | | | | | | | | | | |
|---|---|---|---|---|---|---|---|---|---|---|---|---|---|---|---|
| | Full (100 cc) | | | | | Half (50 cc) | | | | | Quarter (25 cc) | | | | |
| Frequency of Change | 1~2 | 3~4 | 5~6 | 7~8 | 9~ | 1~2 | 3~4 | 5~6 | 7~8 | 9~ | 1~2 | 3~4 | 5~6 | 7~8 | 9~ |
| COF. | 1.5 | 3.5 | 5.5 | 7.5 | 10 | 1.5 | 3.5 | 5.5 | 7.5 | 10 | 1.5 | 3.5 | 5.5 | 7.5 | 10 |
| Amount of Urine | 150 | 350 | 550 | 750 | 1000 | 75 | 175 | 275 | 375 | 500 | 37.5 | 87.5 | 137.5 | 187.5 | 250 |

Depending on the disposable absorbent incontinence article which is used, a table which should be referred to is chosen among Tables III (a)-(h). For example, if a user uses a disposable taped diaper (which is a chosen answer to Q13) which is fully wet (which is a chosen answer to Q15) and the frequency for change is 3-4 times (which is a chosen answer to Q14), the estimated total amount of urine discharged for the time period specified by the user is obtained from Table III (a) as 1750 cc. The data of the calculated amount of urine is stored in the system and will be used in the product selection by the system.

The table IV shows a general data structure of a product selection matrix which is preferably used by the system for the product selection.

The possible answers PA, for each question, are preliminarily programmed to the answer cells A(1,1)-A(m,10) as conditions in accordance with a predetermined product selection guideline so that each answer sell can hit if the user's answer meets the conditions (i.e., the possible answer programmed in the answer cell). Such a predetermined product selection guideline should be well designed so that they can provide a product selection for disposable absorbent incontinence articles which meets the user's individual needs.

In operation, if the answers of a user meets (or hits) all (or at least the majority of) the conditions in one column, for example, the column of A(1,3), the combination of the products X1 and Y3 is selected and recommended by the system.

TABLE IV

| Product X | | X1 | | | X2 | | | | | Xk |
|---|---|---|---|---|---|---|---|---|---|---|
| Product Y | Y1 | Y2 | Y3 | Y4 | Y5 | Y6 | ... | ... | ... | Yn |
| Q1 | A(1,1) | A(1,2) | A(1,3) | A(1,4) | ... | ... | ... | ... | ... | A(1,n) |
| Q2 | A(2,1) | A(2,2) | A(2,3) | ... | ... | ... | ... | ... | ... | A(2,n) |
| Q3 | A(3,1) | A(3,2) | ... | ... | ... | ... | ... | ... | ... | ... |
| Q4 | A(4,1) | ... | ... | ... | ... | ... | ... | ... | ... | ... |
| . | . | . | . | . | . | . | . | . | . | . |
| . | . | . | . | . | . | . | . | . | . | . |
| . | . | . | . | . | . | . | . | . | . | . |
| Qm | A(m,1) | A(m,2) | ... | ... | ... | ... | ... | ... | ... | A(m,n) |

By referring to this type of product selection matrix, the system selects and recommends a preferred disposable absorbent incontinence article or a preferred combination of two disposable absorbent incontinence articles. Each of the product cells X1-Xk and Y1-Yn corresponds to one disposable absorbent incontinence article (of a specific type (or size) or if desired). If appropriate, some of the product cells X1-Xk may correspond to the other articles than disposable absorbent incontinence article (e.g., a stretch pant and a underwear). The questions Q1-Qm in this table correspond to the questions Q1-Qm described in Table I. This matrix includes answer cells A(1,1)-A(m,10) each containing conditions which are used for selecting disposable absorbent article(s), i.e., X1-X4 and Y1-Y10, by the system.

In the preferred embodiment which has the 22 predetermined questions and predetermined possible answers PA described by Tables II (a)-(j), the predetermined possible answers PA are programmed to the answer cells A(1,1)-A(m, 10) before the system starts the product selection. Tables V (a)-(f) show a preferred example of the product selection matrix which can be used in one preferred embodiment.

TABLE V (a)

| Product X | | X1 | |
|---|---|---|---|
| Product Y | Y1 | Y2 | Y3 |
| Q1 | All | All | All |
| Q2 | PA(2,1) | PA(2,1) | PA(2,1) |
| Q3 | All | All | All |

TABLE V (a)-continued

| Product X<br>Product Y | X1<br>Y1 | Y2 | Y3 |
| --- | --- | --- | --- |
| Q4 | PA(4,1), PA(4,3) | PA(4,1), PA(4,3) | PA(4,1), PA(4,3) |
| Q5 | PA(5,1)-PA(5,4) | PA(5,1)-PA(5,4) | PA(5,1)-PA(5,4) |
| Q6 | All | All | All |
| Q7 | PA(7,2), PA(7,3) | All | All |
| Q8 | All | All | All |
| Q9 | PA(9,1), PA(9,3) | PA(9,1), PA(9,3) | PA(9,1), PA(9,3) |
| Q10 | PA(10,1)-PA(10,3) | All | PA(10,1)-PA(10,3) |
| Q11 | All | All | All |
| Q12 | PA(12,1), PA(12,2) | PA(12,1)-PA(12,4) | PA(12,1), PA(12,2) |
| Q13 | PA(13,1)-PA(13,6) | PA(13,1)-PA(13,6) | PA(13,1)-PA(13,6) |
| Q17 | More than 300 | 100-300 | More than 400 |
| Q18 | PA(18,2) | All | All |
| Q19 | All | All | All |
| Q20 | PA(20,1)-PA(20,3) | PA(20,1)-PA(20,3) | PA(20,1)-PA(20,3) |
| Q21 | PA(21,1)-PA(21,2) | PA(21,1)-PA(21,2) | PA(21,1)-PA(21,2) |
| Q22 | PA(22,1)-PA(22,3) | PA(22,1)-PA(22,3) | PA(22,1)-PA(22,3) |

TABLE V (b)

| Product X<br>Product Y | X2<br>Y4 | Y5 | Y6 |
| --- | --- | --- | --- |
| Q1 | All | All | All |
| Q2 | PA(2,1) | PA(2,1) | PA(2,1) |
| Q3 | All | All | All |
| Q4 | All | All | All |
| Q5 | PA(5,3)-PA(5,6) | PA(5,3)-PA(5,6) | PA(5,3)-PA(5,6) |
| Q6 | All | All | All |
| Q7 | PA(7,3) | PA(7,3) | PA(7,3) |
| Q8 | PA(8,3) | PA(8,3) | PA(8,3) |
| Q9 | PA(9,1), PA(9,3) | PA(9,1), PA(9,3) | PA(9,1), PA(9,3) |
| Q10 | PA(10,1)-PA(10,3) | PA(10,1)-PA(10,3) | PA(10,1)-PA(10,3) |
| Q11 | All | All | All |
| Q12 | PA(12,1), PA(12,2) | PA(12,1)-PA(12,4) | PA(12,1), PA(12,2) |
| Q13 | PA(13,1)-PA(13,6) | PA(13,1)-PA(13,6) | PA(13,1)-PA(13,6) |
| Q17 | More than 300 | 200-400 | More than 400 |
| Q18 | PA(18,2) | All | All |
| Q19 | All | All | All |
| Q20 | PA(20,4)-PA(20,6) | PA(20,4)-PA(20,6) | PA(20,4)-PA(20,6) |
| Q21 | PA(21,2)-PA(21,4) | PA(21,2)-PA(21,4) | PA(21,2)-PA(21,4) |
| Q22 | PA(22,2)-PA(22,4) | PA(22,2)-PA(22,4) | PA(22,2)-PA(22,4) |

TABLE V (c)

| Product X<br>Product Y | X3<br>Y7 | Y8 | Y9 |
| --- | --- | --- | --- |
| Q1 | All | All | All |
| Q2 | PA(2,1) | PA(2,1) | PA(2,1) |
| Q3 | All | All | All |
| Q4 | All | All | All |
| Q5 | PA(5,3)-PA(5,6) | PA(5,3)-PA(5,6) | PA(5,3)-PA(5,6) |
| Q6 | All | All | All |
| Q7 | PA(7,3) | PA(7,3) | PA(7,3) |
| Q8 | PA(8,3) | PA(8,3) | PA(8,3) |
| Q9 | PA(9,1), PA(9,3) | PA(9,1), PA(9,3) | PA(9,1), PA(9,3) |
| Q10 | PA(10,1)-PA(10,3) | PA(10,1)-PA(10,3) | PA(10,1)-PA(10,3) |
| Q11 | All | All | All |
| Q12 | PA(12,1), PA(12,2) | PA(12,1)-PA(12,4) | PA(12,1), PA(12,2) |
| Q13 | PA(13,1)-PA(13,6) | PA(13,1)-PA(13,6) | PA(13,1)-PA(13,6) |
| Q17 | Less than 200 | 100-300 | More than 400 |
| Q18 | PA(18,2) | All | All |
| Q19 | All | All | All |
| Q20 | PA(20,4)-PA(20,6) | PA(20,4)-PA(20,6) | PA(20,4)-PA(20,6) |
| Q21 | PA(21,2)-PA(21,4) | PA(21,2)-PA(21,4) | PA(21,2)-PA(21,4) |
| Q22 | PA(22,2)-PA(22,4) | PA(22,2)-PA(22,4) | PA(22,2)-PA(22,4) |

TABLE V (d)

| Product X<br>Product Y | X4<br>Y10 | Y11 | Y12 |
| --- | --- | --- | --- |
| Q1 | All | All | All |
| Q2 | PA(2,1) | PA(2,1) | PA(2,1) |
| Q3 | PA(3,1), PA(3,2) | PA(3,1), PA(3,2) | PA(3,1), PA(3,2) |
| Q4 | PA(4,1), PA(4,3) | PA(4,1), PA(4,3) | PA(4,1), PA(4,3) |
| Q5 | PA(5,1)-PA(5,3) | PA(5,1)-PA(5,3) | PA(5,1)-PA(5,3) |
| Q6 | All | All | All |
| Q7 | All | All | All |
| Q8 | All | All | All |
| Q9 | All | All | All |
| Q10 | PA(10,1)-PA(10,3) | PA(10,1)-PA(10,3) | PA(10,1)-PA(10,3) |
| Q11 | All | All | All |
| Q12 | PA(12,1), PA(12,2) | PA(12,1)-PA(12,4) | PA(12,1), PA(12,2) |
| Q13 | PA(13,1)-PA(13,6) | PA(13,1)-PA(13,6) | PA(13,1)-PA(13,6) |
| Q17 | Less than 250 | 100-300 | More than 400 |
| Q18 | All | All | All |
| Q19 | All | All | All |
| Q20 | PA(20,1)-PA(20,3) | PA(20,1)-PA(20,3) | PA(20,1)-PA(20,3) |
| Q21 | PA(21,1), PA(21,2) | PA(21,1), PA(21,2) | PA(21,1), PA(21,2) |
| Q22 | PA(22,1)-PA(22,3) | PA(22,1)-PA(22,3) | PA(22,1)-PA(22,3) |

TABLE V (e)

| Product X<br>Product Y | X5<br>Y13 | Y14 |
| --- | --- | --- |
| Q1 | PA(1,2) | All |
| Q2 | PA(2,1) | PA(2,1) |
| Q3 | PA(3,2)-PA(3,4) | PA(3,2)-PA(3,4) |
| Q4 | All | All |
| Q5 | PA(5,3)-PA(5,6) | PA(5,3)-PA(5,6) |
| Q6 | All | All |
| Q7 | PA(7,2), PA(7,3) | PA(7,2), PA(7,3) |
| Q8 | PA(8,3) | PA(8,3) |
| Q9 | PA(9,1) | PA(9,1) |
| Q10 | All | All |
| Q11 | PA(11,2)-PA(11,4) | PA(11,1)-PA(11,3) |
| Q12 | PA(12,3)-PA(12,6) | PA(12,1), PA(12,2) |
| Q13 | All | PA(13,1)-PA(13,6) |
| Q17 | Less than 200 | More than 300 |
| Q18 | All | All |
| Q19 | All | All |
| Q20 | PA(20,6) | PA(20,6) |
| Q21 | PA(21,4) | PA(21,4) |
| Q22 | PA(22,5) | PA(22,5) |

TABLE V (f)

| Product X | X6 | | |
|---|---|---|---|
| Product Y | Y15 | Y16 | Y17 |
| Q1 | PA(1,2) | All | All |
| Q2 | PA(2,1) | PA(2,1) | PA(2,1) |
| Q3 | PA(3,3), PA(3,4) | PA(3,3), PA(3,4) | PA(3,3), PA(3,4) |
| Q4 | All | All | All |
| Q5 | PA(5,3)-PA(5,6) | PA(5,3)-PA(5,6) | PA(5,3)-PA(5,6) |
| Q6 | All | All | All |
| Q7 | PA(7,2), PA(7,3) | PA(7,2), PA(7,3) | PA(7,2), PA(7,3) |
| Q8 | PA(8,3) | PA(8,3) | PA(8,3) |
| Q9 | PA(9,1) | PA(9,1) | PA(9,1), PA(9,3) |
| Q10 | All | All | PA(10,1)-PA(10,3) |
| Q11 | PA(11,2)-PA(11,4) | PA(11,2)-PA(11,4) | All |
| Q12 | PA(12,3)-PA(12,6) | PA(12,3)-PA(12,6) | PA(12,1), PA(12,2) |
| Q13 | All | All | PA(13,1)-PA(13,6) |
| Q17 | Less than 70 | Less than 150 | 150-300 |
| Q18 | All | All | All |
| Q19 | All | All | All |
| Q20 | PA(20,6) | PA(20,6) | PA(20,6) |
| Q21 | PA(21,4) | PA(21,4) | PA(21,4) |
| Q22 | PA(22,5) | PA(22,5) | PA(22,5) |

In Tables V (a)-(f), the product cells X1-X6 correspond to the following incontinence devices which are preferably used as an outer article: X1: a disposable taped diaper; X2: a disposable pull-on diaper ("severe" or "nighttime use"); X3: a disposable pull-on diaper ("light" or "daytime use"); X4: a disposable flat pad (or a diaper cover); X5: a stretch pant; and X6: a underwear. The product cells Y1-Y17 correspond to the following incontinence devices (or no devices) which are preferably used as an inner article: Y1: no inner device; Y2: a disposable urine incontinence pad ("regular" or "super"); Y3: a disposable urine incontinence pad ("big" or "wide"); Y4: no inner device; Y5: a disposable urine incontinence pad ("regular" or "super"); Y6: a disposable urine incontinence pad ("big" or "wide"); Y7: no inner device; Y8: a disposable urine incontinence pad ("regular" or "super"); Y9: a disposable urine incontinence pad ("big" or "wide"); Y10: no inner device; Y11: a disposable urine incontinence pad ("regular" or "super"); Y12: a disposable urine incontinence pad ("big" or "wide"); Y13: a disposable urine incontinence pad having a lower absorbent capacity (i.e., less than 150 cc) such as "Certina Anshin Shisuu 1.2" which is marketed by Procter & Gamble Far East, Inc. in Japan; Y14: a disposable urine incontinence pad having a higher absorbent capacity such as "Certina Anshin Shisuu 3.4" which is marketed by Procter & Gamble Far East, Inc. in Japan; Y15: a guard; Y16: a disposable urine incontinence pad ("regular" or "super"); and Y17: a disposable urine incontinence pad ("big" or "wide").

In Tables V (a)-(f), the term "All" in an answer cell means all possible answers can be filled in the answer cell, i.e., the answer cell having "All" is not used for the product selection. In addition, the question Q17 is for the amount of urine discharged by an incontinent person for the time period specified by the user. The estimated amount of urine discharged by the incontinent person which is obtained by referring to Tables III (a)-(g) is used for the product selection by comparing the same with the conditions for the question Q17.

In operation, if the answers of a user meets (or hits) all (or at least the majority of) the conditions in one column, for example, the column of Y3, the combination of the products X1 and Y3 (i.e., a disposable taped diaper and a disposable urine incontinence pad ("big" or "wide") is selected and recommended by the system.

Figure 3:
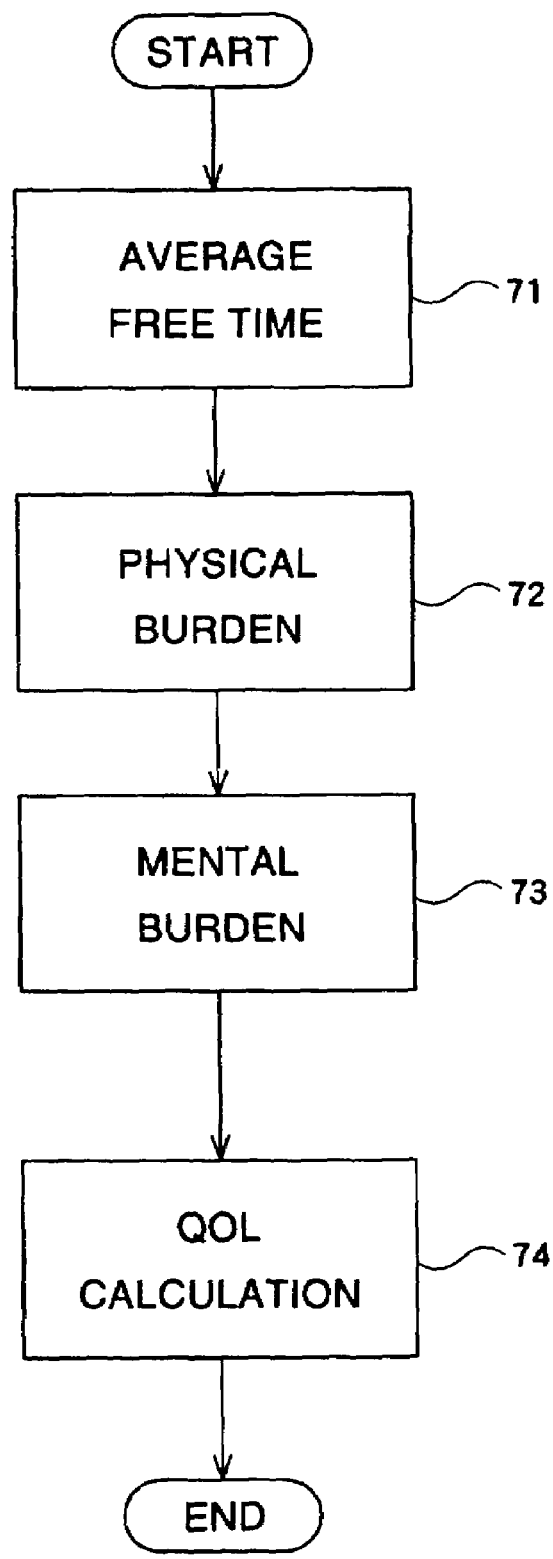
FIG. 3 is a flow chart describing the processes for calculating the value of the quality of life (QOL) of a caregiver which are performed by the product recommendation system shown in FIG. 1.

FIG. 3 is a flow chart describing the processes for calculating the value of the quality of life (QOL) of a caregiver which are performed by the product recommendation system shown in FIG. 1. The quality of life of a caregiver who takes care of an incontinent person is evaluated (or calculated) by the following steps. To receive necessary information from users, the system preferably indicates questions and a plurality of possible answers for each question for selection by the users.

In Step 71, information about an average free time the caregiver can have within a day is received by the system. In general, the availability of the average free time affects several activities in the caregiver's life, for example, going out from home (or leaving home), having personal time, sleeping without being disturbed, washing clothes/sheets; having home helper's services, and the like.

In Step 72, information about a degree of physical burden the caregiver has for taking care of the incontinent person is received by the system. Examples of physical burden include having a waist pain and/or an elbow pain caused by changing disposable absorbent incontinence articles, making and serving meals, and moving an incontinent person (e.g., from a bed to a wheelchair).

In Step 73, information about a degree of mental burden the caregiver has for taking care of the incontinent person is received by the system. Examples of mental burden include concern about malodor at home, and less confidence for taking care of the incontinent person.

In Step 74, the value of the quality of life (QOL) is calculated based on the received information in accordance with a predetermined algorism which is described hereinafter.

The following Tables VI (a)-(c) show an example of questions Q31-Q36 and possible answers PA which are preferably used by the system. It should be noted that these questions and possible answers merely examples, and that depending on the system design one or more of them may be eliminated and other questions and answers can be used as long as they can help the evaluation of the caregiver's quality of life.

TABLE VI (a)

| Q31: Unable to leave home (points) | Q32: Unable to have personal time (points) |
|---|---|
| PA(31,1): definitely agree (5) | PA(32,1): definitely agree (5) |
| PA(31,2): strongly agree (4) | PA(32,2): strongly agree (4) |
| PA(31,3): agree (3) | PA(32,3): agree (3) |
| PA(31,4): slightly agree (2) | PA(32,4): slightly agree (2) |
| PA(31,5): disagree (1) | PA(32,5): disagree (1) |

TABLE VI (b)

| Q33: Unable to sleep without disturbed (points) | Q34: Causing Physical Pain (points) |
|---|---|
| PA(33,1): definitely agree (5) | PA(34,1): definitely agree (5) |
| PA(33,2): strongly agree (4) | PA(34,2): strongly agree (4) |
| PA(33,3): agree (3) | PA(34,3): agree (3) |
| PA(33,4): slightly agree (2) | PA(34,4): slightly agree (2) |
| PA(33,5): disagree (1) | PA(34,5): disagree (1) |

TABLE VI (c)

| Q35: Concerned about malodor at home (points) | Q36: Inconfidence in Taking Care (points) |
|---|---|
| PA(35,1): definitely agree (5) | PA(36,1): definitely agree (5) |
| PA(35,2): strongly agree (4) | PA(36,2): strongly agree (4) |

TABLE VI (c)-continued

| Q35: Concerned about malodor at home (points) | Q36: Inconfidence in Taking Care (points) |
|---|---|
| PA(35,3): agree (3) | PA(36,3): agree (3) |
| PA(35,4): slightly agree (2) | PA(36,4): slightly agree (2) |
| PA(35,5): disagree (1) | PA(36,5): disagree (1) |

In a preferred embodiment, the system indicates these questions and possible answers, and requests user's selection for each question. The point shown in each answer cell is added when the user's answer hits the answer cell. Thus, in total 6 points which are obtained from the answer cells are added thereby producing the value of the caregiver's quality of life (QOL).

The value of the caregiver's quality of life (QOL) is preferably sent to the user through the network. The calculation of the caregiver's quality of life is performed periodically and the value change of the quality of life (QOL) is monitored by the system.

Referring again to FIG. 2, if the value of the caregiver's quality of life (QOL) is below a predetermined level PL, for example 40 points (Step 65), the process returns to Step 61 and necessary processes for further product recommendation are performed by repeating the processes of Steps 61-64. As a result, a new (or modified) product recommendation is obtained and sent to the user through the network.

It is understood that the examples and embodiments described herein are for illustrative purpose only and that various modifications or changes will be suggested to one skilled in the art without departing from the scope of the present invention.

What is claimed is:

1. A method for recommending a disposable absorbent incontinence article to be used by an incontinent person, comprising the steps of:
 (a) providing a product recommendation device;
 (b) inputting information into the product recommendation device about incontinence devices which are currently used by the incontinent person and information about the situation which is experienced by the user;
 (c) processing the information using the product recommendation device;
 (d) providing output in the form of a selection of at least one disposable absorbent incontinence article from a database of predetermined disposable absorbent incontinence articles based on the information processed by the product recommendation device; and
 wherein the step of inputting information comprises the step of indicating a question and a plurality of possible answers for selection and inputting one or more answers to the question.

2. The method of claim 1, wherein the step for providing output in the form of a selection of at least one disposable absorbent incontinence article comprises a step of providing output in the form of a selection of a combination of two disposable absorbent incontinence articles, based on the information inputted, among the predetermined disposable absorbent incontinence articles.

3. The method of claim 1, further comprising the steps of;
 (e) evaluating the quality of life of a caregiver who takes care of the incontinent person, and
 (f) repeating the steps (a), (b) and (c).

4. The method of claim 1, wherein the question for the information about the user's situation is on the ability of body action of the incontinent person.

5. The method of claim 1, wherein the question for the information about the user's situation is on the ability of at least one of hand and finger activity of the incontinent person.

6. The method of claim 1, wherein the question for the information about the user's situation is on the content(s) of leakage of the incontinent person.

7. The method of claim 1, wherein the question for the information about the user's situation is at least one of on the availability and the quality of the caregiving.

8. The method of claim 1, wherein the question for the information about the user's situation is on the amount of urine discharged by the incontinent person for a time period specified by the user.

9. The method of claim 1, wherein the predetermined disposable absorbent incontinence articles include at least two articles which are selected from the group consisting of a disposable taped diaper, a disposable pull-on diaper, a disposable urine incontinence pad, a disposable flat pad, a disposable fecal collector pouch, and a disposable urine collector pouch.

* * * * *

UNITED STATES PATENT AND TRADEMARK OFFICE
CERTIFICATE OF CORRECTION

| | |
|---|---|
| PATENT NO. | : 7,392,200 B2 |
| APPLICATION NO. | : 10/733560 |
| DATED | : June 24, 2008 |
| INVENTOR(S) | : Yukio Heki et al. |

It is certified that error appears in the above-identified patent and that said Letters Patent is hereby corrected as shown below:

Column 7
TABLE II (b), line 2 of the heading Q3, delete "Incontinene" and insert
-- Incontinence --.

Signed and Sealed this

Thirtieth Day of December, 2008

JON W. DUDAS
*Director of the United States Patent and Trademark Office*